(12) United States Patent
Reichman et al.

(10) Patent No.: US 6,461,290 B1
(45) Date of Patent: *Oct. 8, 2002

(54) COLLAPSIBLE ISOLATION APPARATUS

(75) Inventors: David A. Reichman, Gaithersburg, MD (US); Lyn J. Yaffe, Gaithersburg, MD (US); Robert L. Mullins, Jr., Hazelcrest, IL (US)

(73) Assignee: IIT Research Institute, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/660,432

(22) Filed: Sep. 12, 2000

Related U.S. Application Data

(63) Continuation-in-part of application No. 09/379,962, filed on Aug. 24, 1999, now Pat. No. 6,321,764.
(60) Provisional application No. 60/113,503, filed on Dec. 21, 1998.

(51) Int. Cl.[7] ............................................... A61G 10/00
(52) U.S. Cl. .................................. 600/21; 5/626; 5/627; 5/312; 5/6
(58) Field of Search ...................... 600/21–22; 312/1–6; 5/600, 625–628; 128/202.12, 205.26; 135/128

(56) References Cited

U.S. PATENT DOCUMENTS

| | | | |
|---|---|---|---|
| 2,683,262 A | 7/1954 | Foss ................... 2/2 |
| 2,985,129 A | 5/1961 | Kirkpatrick ................ 113/111 |
| 3,118,401 A | 1/1964 | Platt ................ 109/1 |
| 3,119,358 A | 1/1964 | Colson et al. ................. 109/1 |
| 3,265,059 A | 8/1966 | Matthews ....................... 128/1 |
| 3,272,199 A | 9/1966 | Matthews ....................... 128/1 |
| 3,695,507 A | 10/1972 | Sams ........................... 229/53 |
| 3,766,844 A | 10/1973 | Donnelly et al. ............... 98/33 |
| 3,877,427 A | * 4/1975 | Alexeev et al. ................ 600/21 |
| 4,000,749 A | 1/1977 | Busco .......................... 135/1 |
| 4,352,991 A | 10/1982 | Kaufman ......................... 307/9 |
| 4,389,066 A | 6/1983 | Weir et al. ..................... 296/19 |
| 4,584,989 A | 4/1986 | Stith .............................. 128/1 |
| 4,736,762 A | 4/1988 | Wayman ........................ 135/88 |
| 5,061,235 A | * 10/1991 | Hogan ........................... 600/21 |
| 5,255,673 A | * 10/1993 | Cardwell et al. ............. 600/21 |
| 5,314,377 A | 5/1994 | Pelosi .......................... 454/187 |
| 5,331,991 A | 7/1994 | Nilsson ......................... 135/93 |
| 5,582,574 A | * 12/1996 | Cramer ......................... 600/21 |
| 5,626,151 A | 5/1997 | Linden ......................... 128/897 |
| 5,630,296 A | 5/1997 | Kendall ........................ 52/2.11 |
| 5,725,426 A | 3/1998 | Alvarez ....................... 454/187 |
| 5,865,722 A | * 2/1999 | Heng ........................... 600/21 |
| 5,950,625 A | * 9/1999 | Bongiovanni et al. ........ 600/21 |
| 6,241,653 B1 | * 6/2001 | Gauger et al. ................ 600/21 |

* cited by examiner

*Primary Examiner*—John P. Lacyk
(74) *Attorney, Agent, or Firm*—Fitch, Even, Tabin & Flannery

(57) ABSTRACT

A collapsible, transportable personnel isolation apparatus or device is used to isolate a patient in a controlled environment and to protect the patient against biological or chemical hazards during transport of the patient. The collapsible apparatus has a flexible containment wall which is expandable from a collapsed, stored state to an expanded state to receive the patient. At least a portion of the containment wall is clear to allow observation of the patient within an interior region of the device. An air filtration system is provided for filtering air between the airtight interior region and the ambient atmosphere. Preferably, the apparatus has various ports therein, such as glove ports, pass through ports, access ports for cardiac leads, infusion line ports, and ventilation ports. Preferably, an air filtration device provides a flow rate of 4 to 6 cfm to prevent an undesirable build-up of carbon dioxide and provides a predetermined air pressure within the interior regions. In one form, the containment device is a clam shell litter type for transport of a prone patient and in another form the device is a jacket type with a hood defining an air impermeable chamber for an ambulatory patient who carries an ambulatory air filtration device for supplying and filtering the air impermeable chamber.

50 Claims, 11 Drawing Sheets

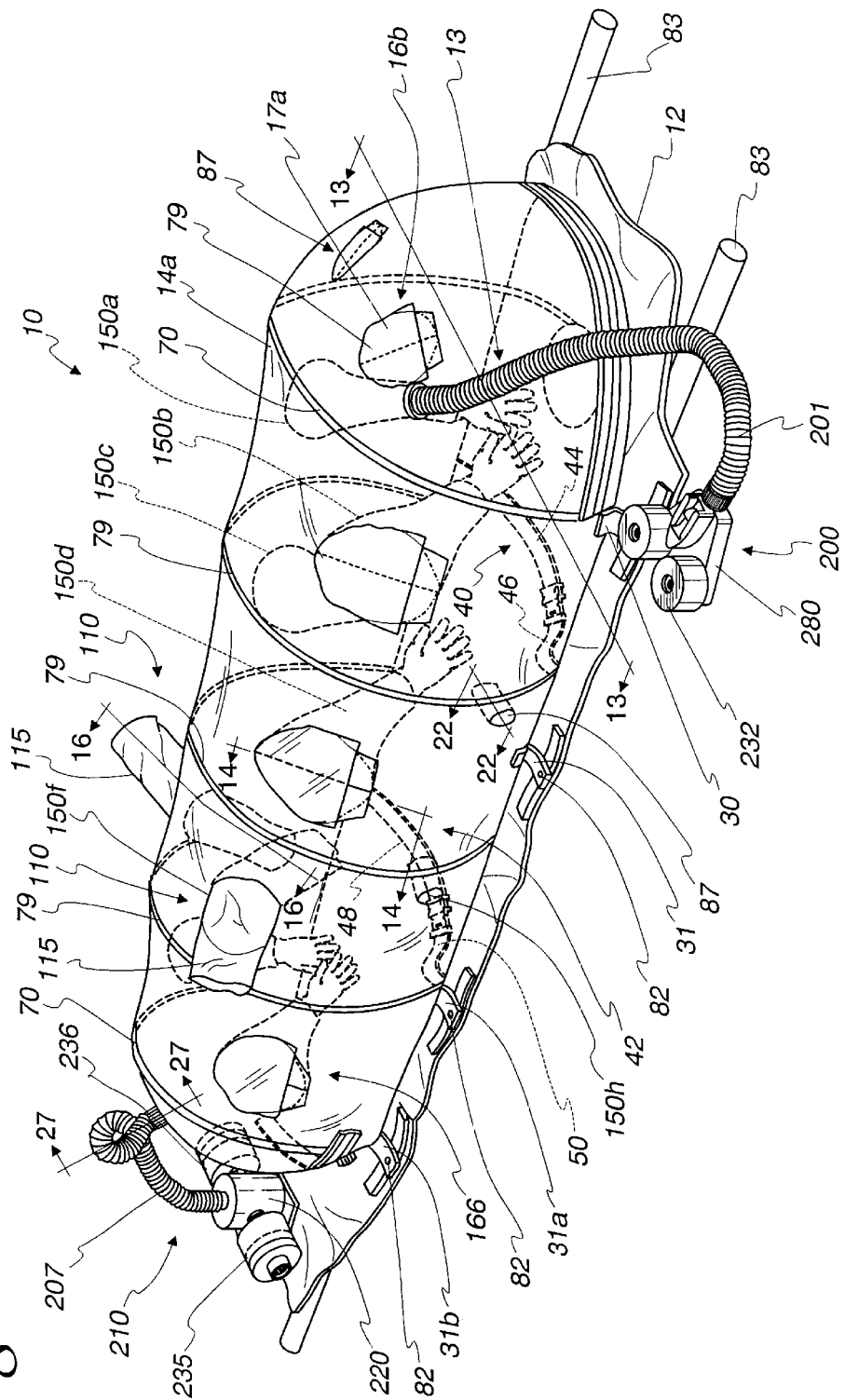

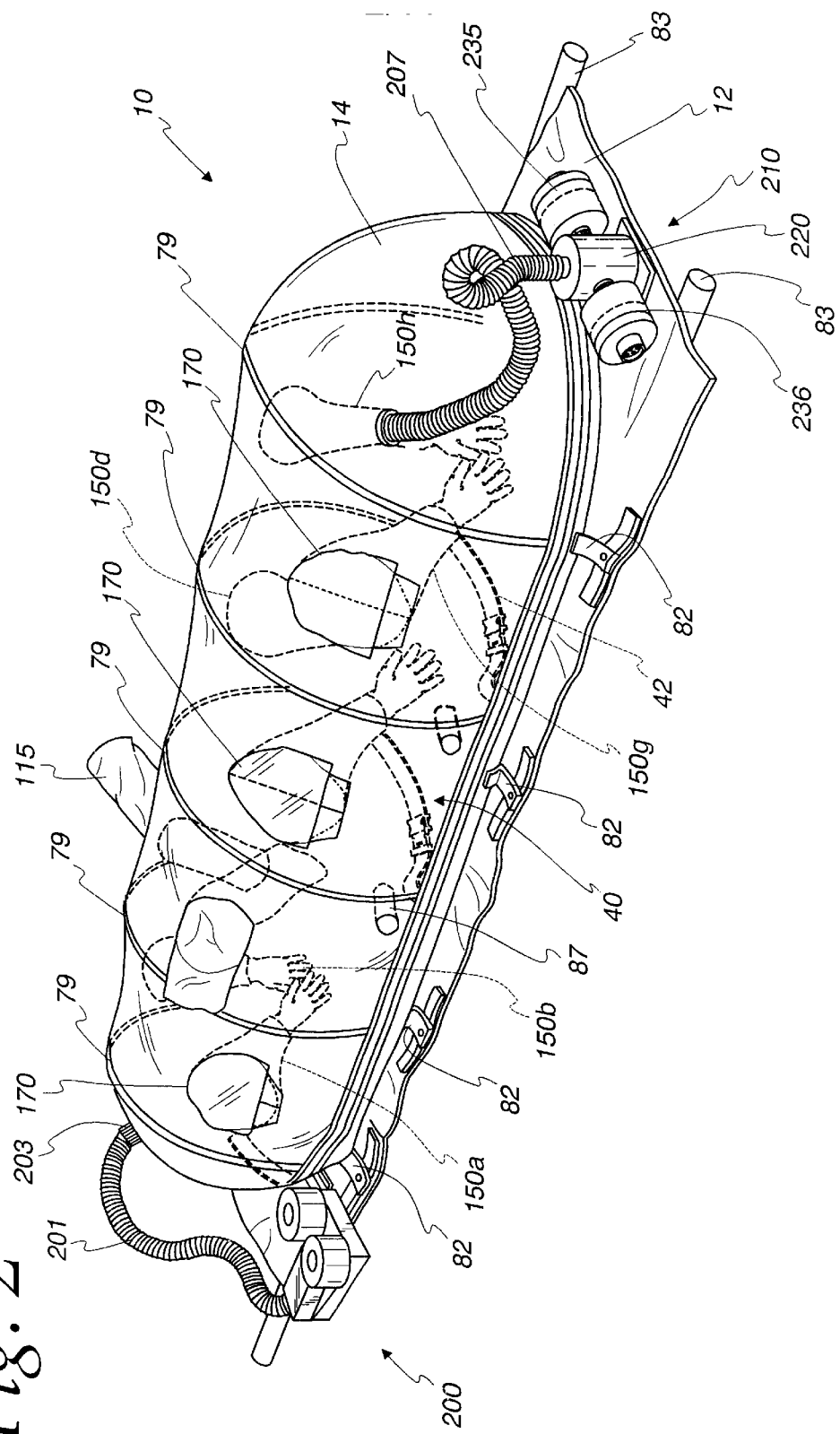

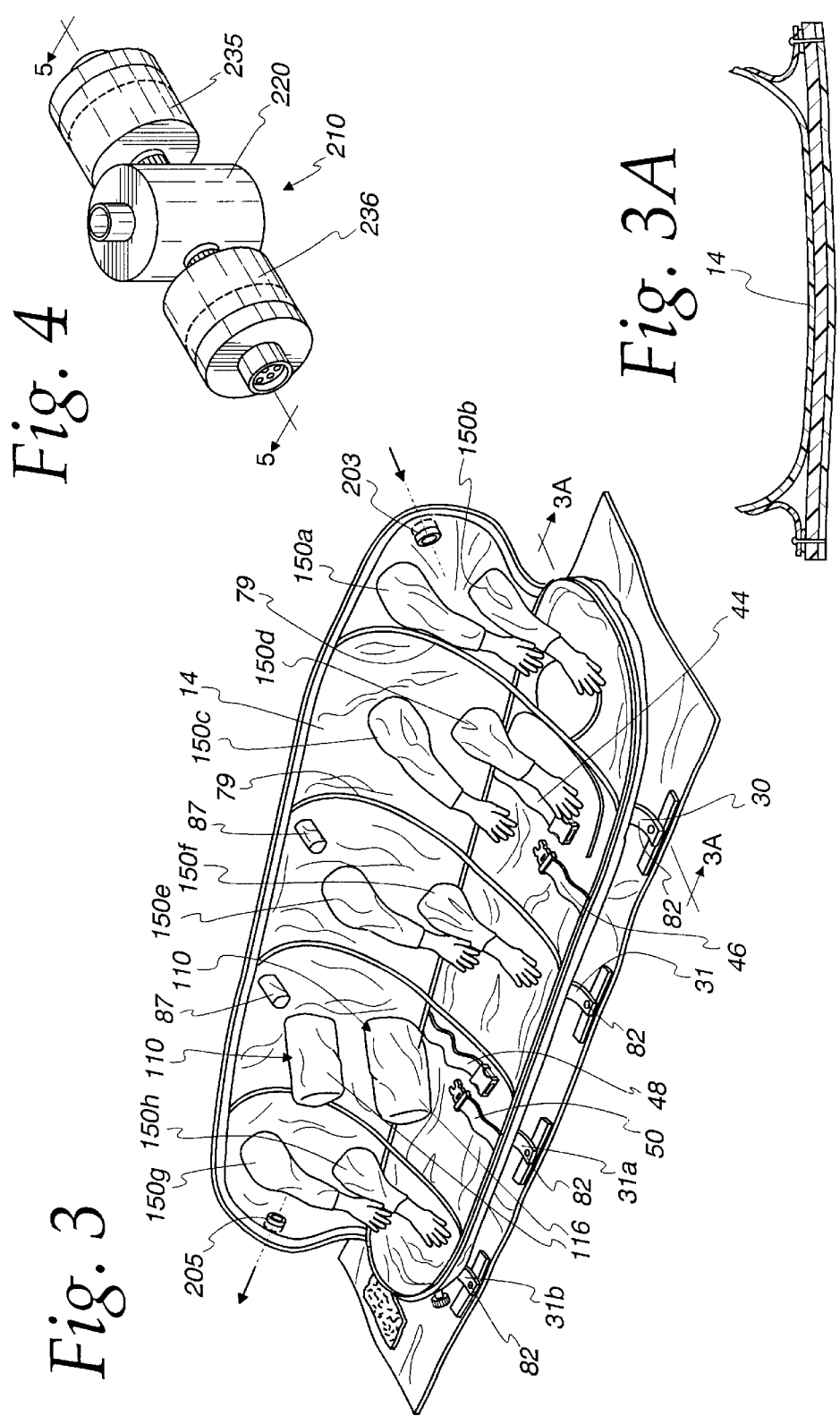

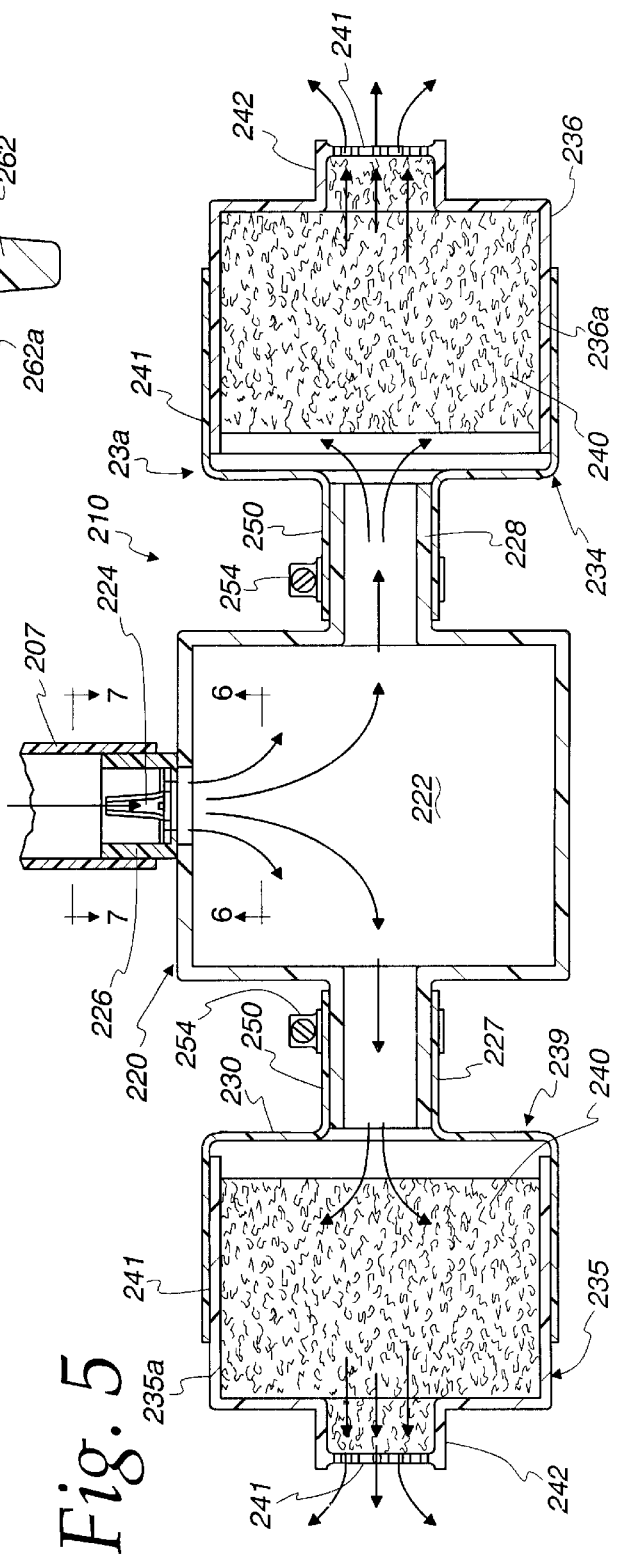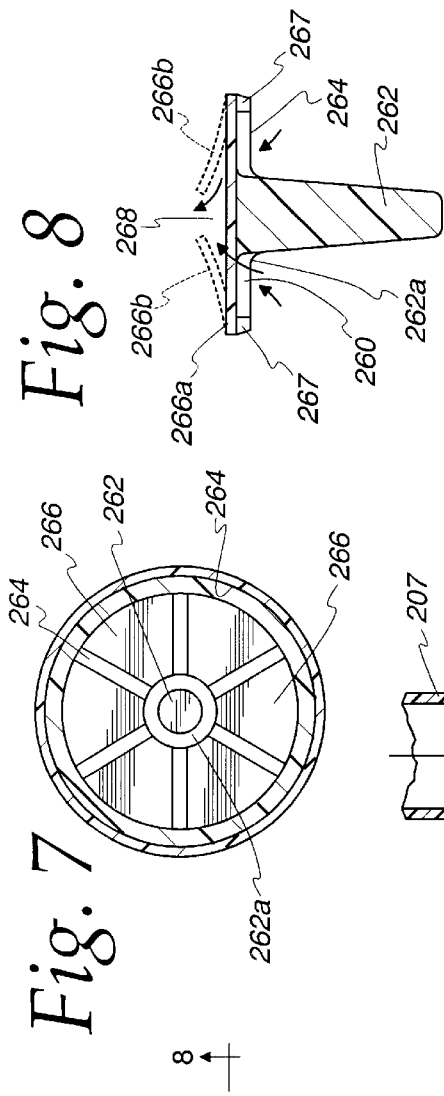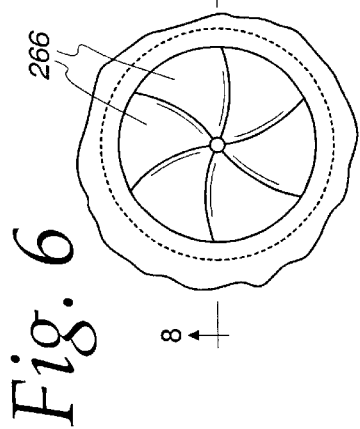

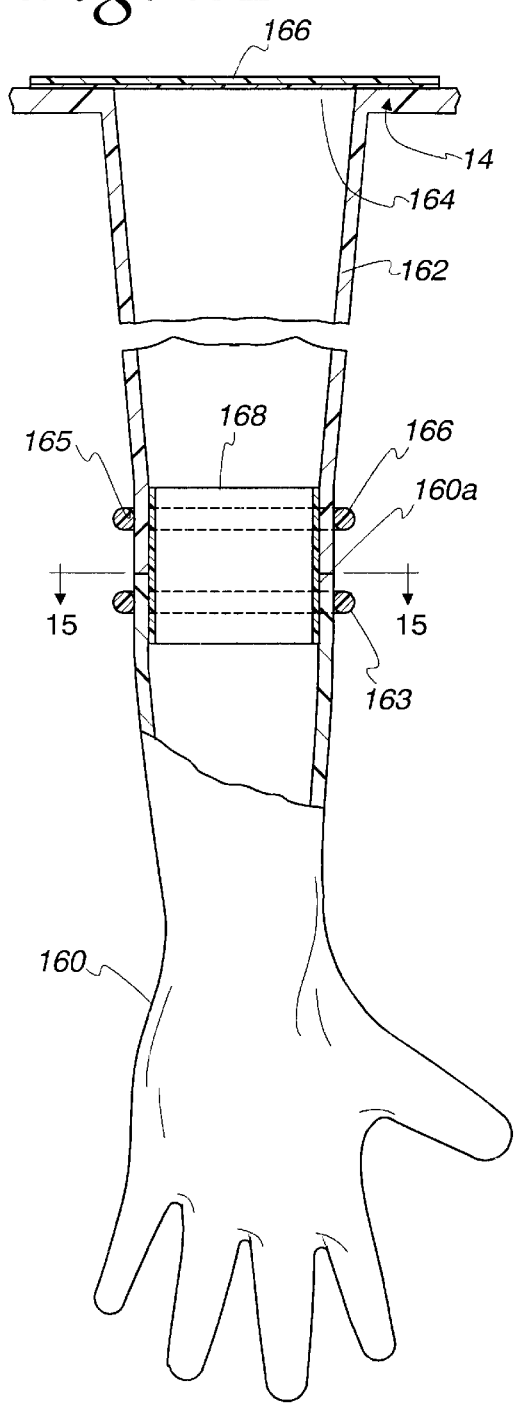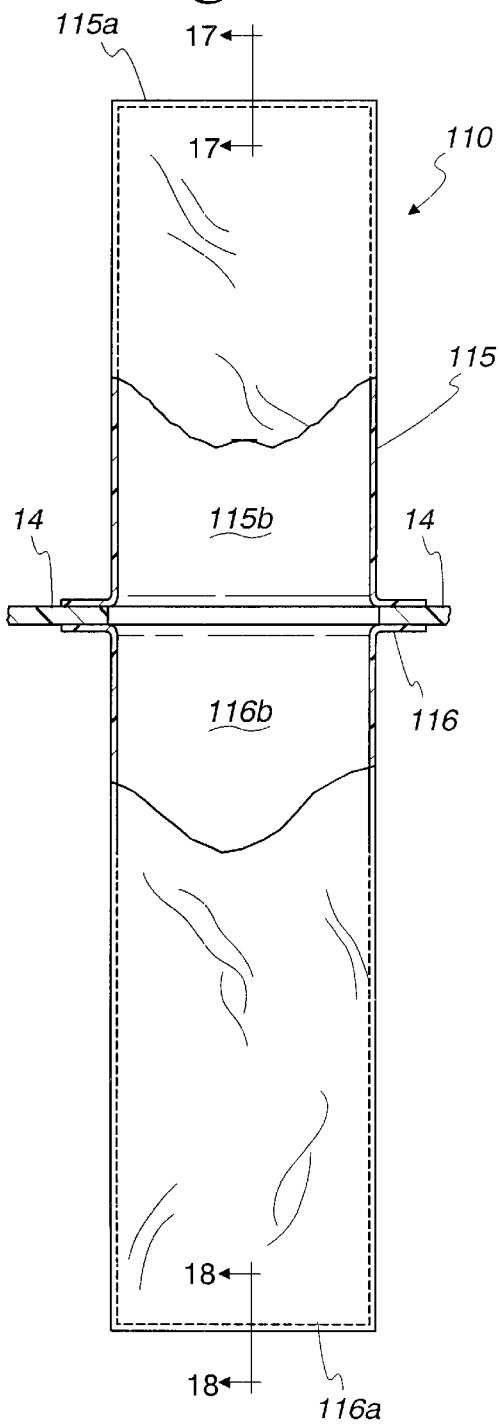

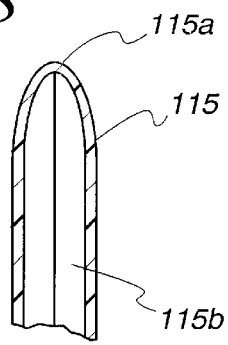
Fig. 17
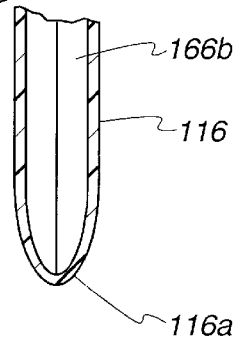
Fig. 18
Fig. 19
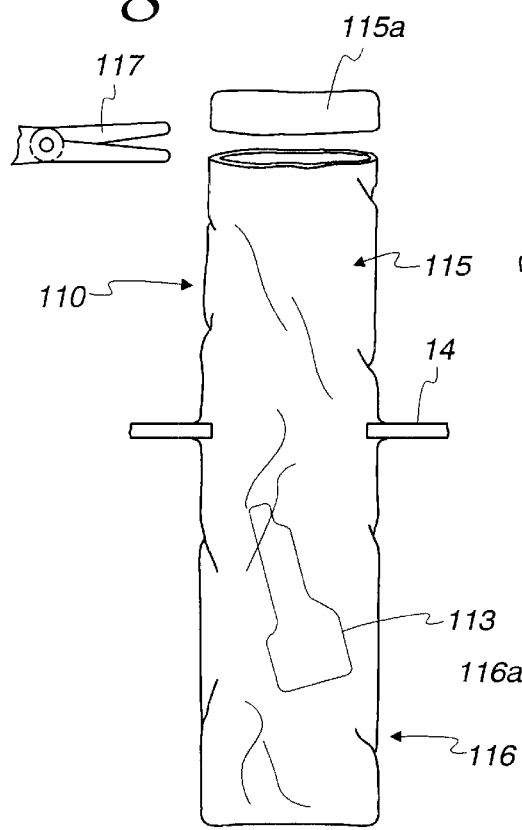
Fig. 20
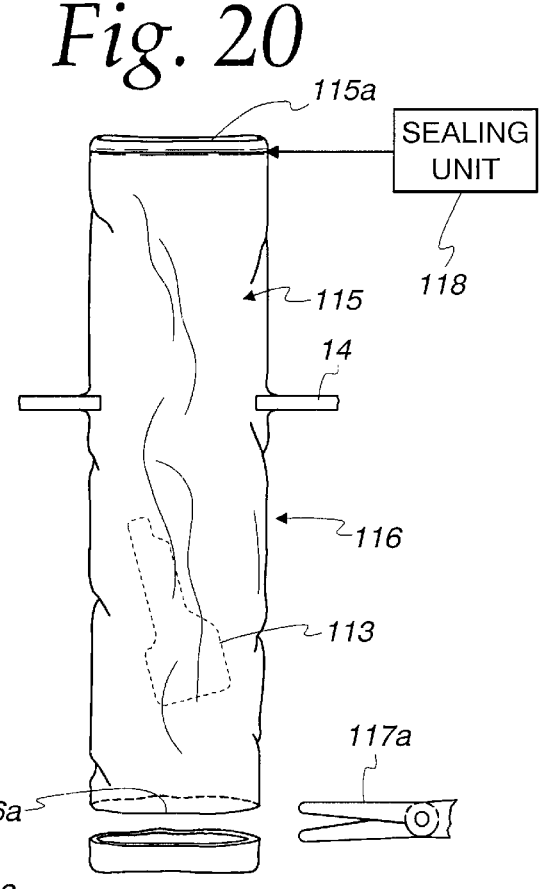

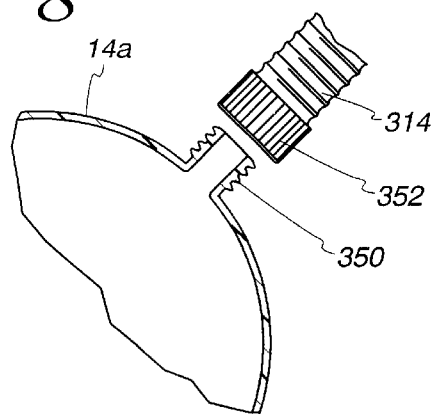
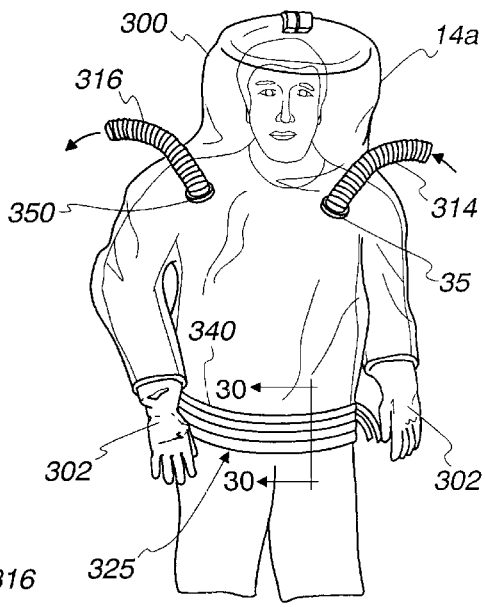
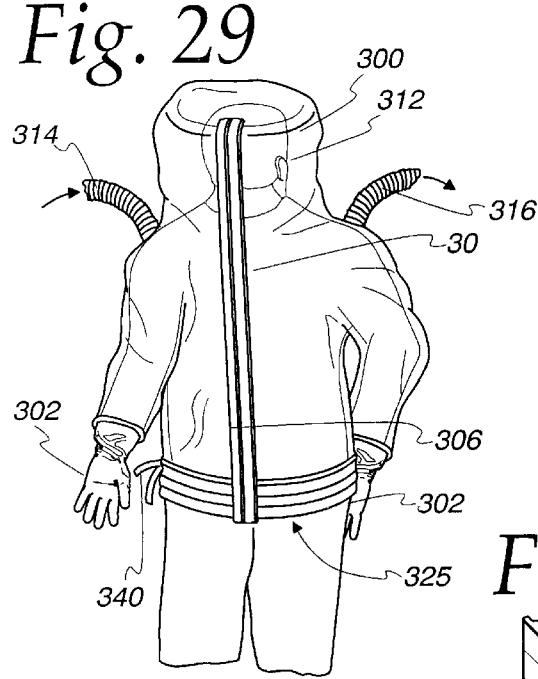
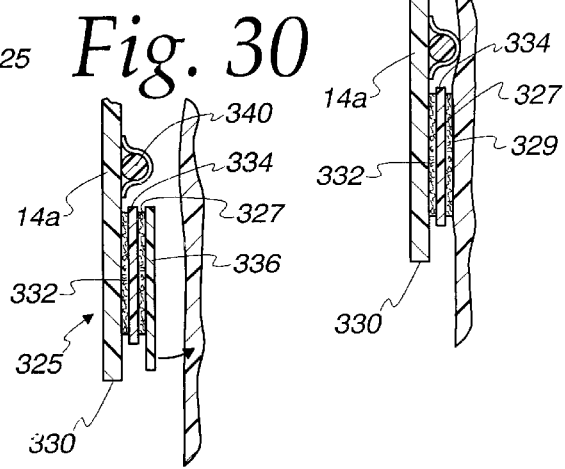

COLLAPSIBLE ISOLATION APPARATUS

CROSS REFERENCE TO RELATED APPLICATIONS

This application is a continuation-in-part of U.S. application Ser. No. 09/379,962, filed Aug. 24, 1999, now U.S. Pat. No. 6,321,764 which claimed priority from U.S. Provisional Application No. 60/113,503, filed Dec. 21, 1998.

GOVERNMENTAL RIGHTS

The subject matter disclosed and claimed herein was developed under the Department of Defense Contract No. DLA900-93-D-0011/0038. The government has certain rights in the invention.

BACKGROUND OF THE INVENTION

This invention relates to isolation pods or protective containment devices used to isolate patients and for their transport. This transportable containment device provides an impermeable barrier against chemical and biological agents by isolating the injured person within a plastic pressure-type filtered environment, and protects the persons doing the transporting as well as the patient. Preferably the isolation device is capable of being compactly stored and/or easily transported to a site for use in emergencies For instance, large containers or packs may store a large number of such containment devices for use by military people in the field against biological or other type of chemical hazards. On the other hand, individual isolation devices may be conveniently carried or stored on a paramedic emergency vehicle for use in emergencies when transporting one or more infectious patients or person that has AIDS or unknown infectious diseases that need to be controlled against transmission to the people doing the transporting.

The illustrated and preferred isolation and protective device is for use with a litter or stretcher, or other device, which allows the protective barrier to primarily be made of a thin plastic material which is collapsed for compact storage and expanded to receive a patient thereby providing a low-cost, disposable, containment device. For military applications, there is a need for a drag bottom for use with the isolation device so that the patient can be carried or dragged by a corpsman or a paramedic across a battlefield to a vehicle for later transport to a hospital, or the like. Another important consideration in the use of such a isolation device is that it be simple to use in times of extreme emergency or excitability, such that personnel opening the device and placing people into the containment device, may not be thinking as clearly as they would normally be thinking and such that untrained personnel may be pressed into service for placing patients in these isolation devices when there is a wide-spread, mass chemical or biological attack. Also, in the case of some diseases, such as hemorrhagic fevers, like Ebola or Marburg viruses, the patients may resist handling and there is a risk in contaminating the handlers unless the device is capable of being opened to a position in which it is very easy to place the patient inside. Further, when the patient is inside, it is important that the patient not be feeling claustrophobic and, therefore, it is desirable to provide the patient with a clear field of view, as well as to have air flowing the patient's face so that the patient understands that he has plenty of air to breathe while being surrounded by the barrier housing.

With respect to air ventilation, when the ambient atmosphere about the patient is contaminated, the air being supplied into the containment device should be purified or filtered before flowing across the patient in the protective containment device. Stated differently, if the surrounding ambient atmosphere is contaminated, then it is desired than the patient be placed within the containment device, and that the air being supplied to the patient be purified and filtered before it is forced into the containment device. On the other hand, if the has an infectious disease that can be transported by air, then it is desired to have the air filtered or purified before it is discharged from the interior of the protective device into the ambient atmosphere. Also, there are a number of other considerations with respect to air flow that should be met to provide a viable air flow dynamics and an air-tight environment about the patient.

From a cost and a weight standpoint, there is currently provided a Vickers box device which typically cost $20,000 to $30,000 and is heavy, in that it weighs about 200 pounds unloaded. Such a device is very difficult to store in that it is bulky and not adapted for storage in large number or for use in the event of a biological emergency. In addition, it cannot be transported in various types of military evacuation vehicles or used with the common paramedic vehicles used by fire departments or other health safety units of a municipality. The Vickers box is intended for use for transporting victims of natural biological hazards, such victims may include persons who have been infected with Ebola or Marburg virus, anthrax or the like. The Vickers box comprises a relatively self-contained unit having an external frame with a biological hazard barrier comprising sheet polyvinyl chloride sheet suspended therefrom. The frame has a foot rest or step. A lower substantially oval loading port provides access to the interior through which a patient may be carried to rest on a stretcher-like structure. The barrier has a ventilation tube entering its foot end. Glove ports are formed on the sides of the frame thereof. A pass-through port extends through the barrier approximately near the center of the pod or about waist-high on the patient. There are pairs of glove ports on each side of the unit. Intravenous bags and the like may be suspended from the frame of the unit. An intravenous line may extend through a port in the side of the unit.

The use of flexible plastic, such as PVC for forming a isolation cylindrical plastic tube about a patient and for purifying the air being admitted into the enclosed volume is disclosed in U.S. Pat. Nos. 3,265,059 and 3,272,199. In these patents, a plastic polyvinyl chloride sheet, twice as long as the length of the patient's bed, is hung on a series of slidable supports or by hangers slidable on an overhead external rod so that the medical person with his hands in the glove ports may administer to the patient by sliding the flexible sheet between the patient's head and feet with the plastic sliding and the hangers sliding along the top support rail. In the U.S. Pat. No. 3,265,059, the sheet is folded with creases therein to facilitate its sliding. In the U.S. Pat. No. 3,272,199, air bearings at the end allow the telescoping of the plastic sheet over end units. The devices shown in these patents are for use with hospital beds or the like, and require large external frames having an overhead slide rod. Also, an excessive amount of plastic is used, that is, the plastic sheet is double the amount needed for the length of the patient or mattress. The devices proposed in these patents are bulky and are simply not compact for storage in large numbers to be ready for use in case of a biological emergency, nor are these devices adapted to be used with a litter for transport to or for use within evacuation vehicles, either of the military type or of a fire department type.

What is needed and desired is an inexpensive, easily-compatible and stored isolation device which can be held in inventory by military or civilian defense organizations at various locations for quick access. Also, there is a need for inexpensive and compact isolation devices for inventory by fire departments or other evacuation municipal units where they may be transporting people with airborne infectious diseases or fluid transmitted diseases such as AIDS or hepatitis and where there is bleeding. A large amount of money is spent cleaning emergency vehicles after the transporting of people who are bleeding and who could possibly have AIDS, infectious hepatitis, etc. The amount of time consumed in cleaning such vehicles; and the resultant hazards involved with any improper cleaning to the paramedics and to subsequent patients is a problem. It would be better if the patient could be placed in the isolation containment device and transported without contaminating the evacuation vehicle such that the isolation device, or pod, itself could be disposed of by burning or by cleaning in some manner for reuse.

While the aforesaid copending application describes and illustrates an embodiment in which there is provided a drag bottom and a stretcher, there are other instances where a litter need not be used and that the patient is fully ambulatory and still needs the protection of a containment device. Thus, the present invention is directed to providing the need for such a isolation or containment pod device for an ambulatory or non-ambulatory patient.

SUMMARY OF THE INVENTION

This invention relates to a new and improved collapsible, transportable personnel isolation apparatus which minimizes the biological or chemical hazards to or from a patient within the protective containment apparatus.

The collapsible, transportable containment apparatus may be used with ambulatory patients in one embodiment or used with non-ambulatory patients in another embodiment. The containment device is preferably inexpensive in the sense that it can be purchased and stored by the military and/or by fire or civil defense departments in large quantities for use in terrorist attacks and, after use, may be disposed of by burning or the like. The collapsible, compact nature of the protective containment device allows it to be stored in large numbers on pallets or to require such a small storage space that it can be stored on a civilian or miliary evacuation vehicle and be ready for use when needed.

In the preferred embodiment, the protective containment device is provided with various ports, for example glove ports, pass-through ports, access ports for electrocardiac leads, a stethoscope, or a suction pump line, or infusion line ports for infusion lines that are connected to an external intravenous infusion device. Other ports may be provided for extending a ventilation tube to an airway made into the patient's trachea to intubate the patient. Preferably, sufficient glove ports are provided to allow medical personnel access to the patient's head, chest, abdomen and lower extremities.

In one embodiment of the invention, the isolation device may be used with or as a litter or stretcher with the patient being prone within a thin, plastic housing which is reinforced by strategically-placed straps that will carry the weight of the patient without tearing the plastic housing which, by itself, lacks sufficient strength to support the weight of the patient. Also, in accordance with the preferred embodiment of the invention, a detachable drag bottom or base may be attached to the bottom of the flexible housing to allow dragging of the containment device along the ground for use in situations that necessitate such a the drag bottom was an integral base sheet that is thicker than the flexible housing wall; and the base sheet contained a plurality of handholds therein for carrying the isolation device with the patient therein.

In accordance with another aspect of the invention, the protective isolation device is easily used by trained medical personnel, as well as untrained or unskilled people, because the device is preferably in the shape of a sleeping bag or clam shell having two halves that are easily opened by operation of a closure device, preferably an airtight zipper. The halves are readily laid open and apart to allow the medical personnel to lower the patient onto the lower half in the proper position. In the preferred embodiment, a patient's silhouette is provided on the bottom half showing the location of the patient's head and upper body so that medical personnel, which may be operating under extreme duress or very adverse conditions, can quickly place the patient in the desired orientation. Some patients infected by hemorrhagic fevers, such as Ebola or Marburg virus, may resist handling and others may be thrashing about for various reasons. Preferably, restraints are provided to restrain the patient at the desired position with the protective containment housing for use, if they are needed.

Another important aspect of the invention is to alleviate the patient's apprehension or claustrophobic feeling while within the isolation device. To this end, the patient has a clear view through the transparent, plastic housing and a noticeable flow of air passes across the patient's head. Also, the patient will not feel so encapsulated because this flowing pressurized air, as well as stays or supports, will keep the plastic housing spaced upwardly from contacting with the patient's skin and wounds so that the wounds can be more easily treated. The preferred airflow rate across the patient is 4–6 cfm at a pressure of 4 inches of water, which is needed to prevent buildup of carbon dioxide about the patient's head and to remove moisture that would fog the interior of the plastic housing and thereby interfere with the patient's view of the exterior, as well as the view of the medical personnel into the interior of the containment device.

In accordance with the invention, the dynamics of the airflow and the tightness of the housing against air leakage is such that upon stopping the airflow into the housing, the air pressure within the housing will not decrease by more than twenty percent over a five minute period. Unidirectional airflow valves at the air inlet and exhaust ports prevent air outflow through the inlet and/or the wrong direction through the exhaust ports; and the use of an airtight zipper allows meeting of this air leakage standard.

Tn accordance with another important aspect of the invention, the air is preferably purified prior to being flowed into the containment device and prior to being exhausted into the ambient atmosphere. In crisis situations, the medical personnel may be unsure as to whether it is the ambient atmosphere that is contaminated or it is the atmosphere within the containment device that is contaminated. In the aforesaid copending patent application, the blower and filter unit could be connected to one end of the containment device housing to blow purified air into the patient within protective housing if the medical personnel thought the ambient air was contaminated. On the other hand, if the medical personnel thought that the patient had an infectious disease or other air-born contaminants, then the blower and filter unit was connected to the other end of the protective housing and negative pressure was provided by the blower unit to suck air from the housing. While such arrangement may be used, it is preferred to provide one-way flow devices and blower/purifier units at both ends of the protective housing to provide a unidirectional flow of purified air into and from the protective housing.

In some emergency situations, patients may have extreme burns over large portions of their body, and it may be desirable to place them in a hyper oxygenated atmosphere where the excess oxygen assists in the healing process and may adversely affect bacteria or burn contaminants. The contaminant apparatus of the present invention, with suitable safeguards with respect to fire or the like could be used to receive the hyper oxygenated air and to isolate the patient, particularly during transport from the burn site to a burn treatment center. In such instances, the medical manifold would be equipped with a grounding strap that would prevent static electricity buildup between the patient and the static plastic enclosure.

BRIEF DESCRIPTION OF THE DRAWINGS

FIG. 1 is a perspective view of an isolation apparatus for a pod constructed in accordance with the preferred embodiment of the invention;

FIG. 2 is a perspective view looking at the head end of the isolation apparatus of FIG. 1;

FIG. 3 is a view with the isolation apparatus of FIG. 1 open to expose the glove ports and the pass-through tubes and the interior of the isolation pod;

FIG. 3A is a fragmentary, cross-sectional view showing reinforcing straps at the bottom of the pad;

FIG. 4 is a perspective view of the air purifier device used at the exhaust end for exhausting air from the isolation pod;

FIG. 5 is an enlarged, cross-sectional view taken along the line 5—5 of FIG. 4;

FIG. 6 is a plan view of a one way valve;

FIG. 7 is a cross-sectional view of the one way valve of FIG. 6;

FIG. 8 is a cross-sectional view taken along the line 8—8 of FIG. 6;

FIG. 14 illustrates a glove port and glove sleeve constructed in accordance with one embodiment of the invention;

FIG. 16 is an elevational view of the pass-through sleeves on the interior and exterior of the isolation pod wall;

FIG. 17 is a cross-sectional view taken substantially along the line 17—17 of FIG. 16;

FIG. 18 is a cross-sectional view taken along the line 18—18 of FIG. 16;

FIG. 19 is an elevational view which illustrates the severing of an exterior end of the pass-through tube;

FIG. 20 is an elevational view which shows the sealing of the exterior end of the exterior sleeve of the pass-through and the severing of the interior end of the interior sleeve;

FIG. 22 is a cross-sectional view of a sleeve used for catheters or the like;

FIG. 27 is a perspective view which shows a threaded hose connection for an air hose used with the isolation apparatus jacket for ambulatory patients, shown in FIG. 28.

FIG. 28 is a perspective view of a protective isolation apparatus used with a patient who is ambulatory.

FIG. 29 is a rear view of the ambulatory isolation device of FIG. 28.

FIG. 30 is a cross-sectional view illustrating an adhesive tape connection at the waist of the jacket isolation device of FIGS. 28 and 29.

FIG. 31 is a cross-sectional view showing a layer of an adhesive type to the patient's waist and the use of a drawstring to seal the lower end of the jacket isolation to the patient's waist.

DETAILED DESCRIPTION OF THE PREFERRED EMBODIMENTS

Figure 9:
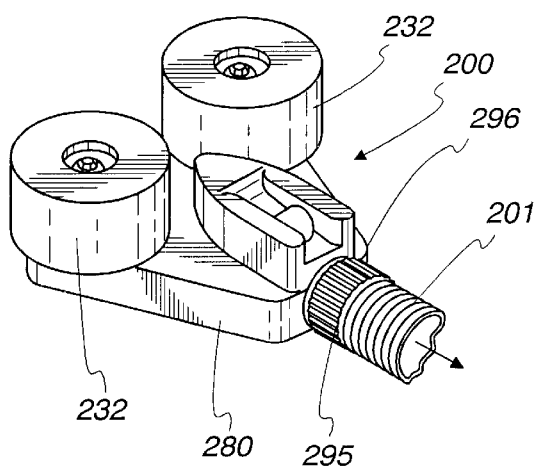
FIG. 9 is an isometric view of the air purifier device for connection to the inlet port of the isolation pod.
Figure 10:
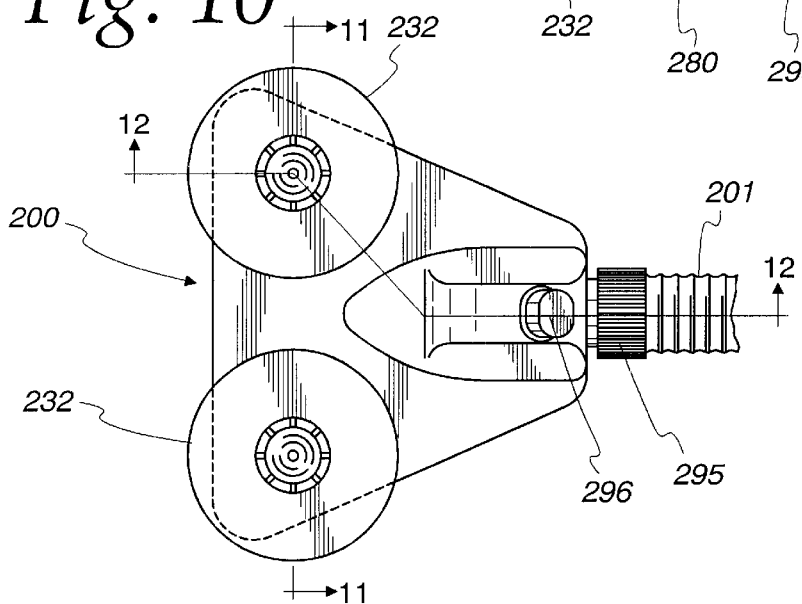
FIG. 10 is a plan view of the air purifier device of FIG. 9.
Figure 11:
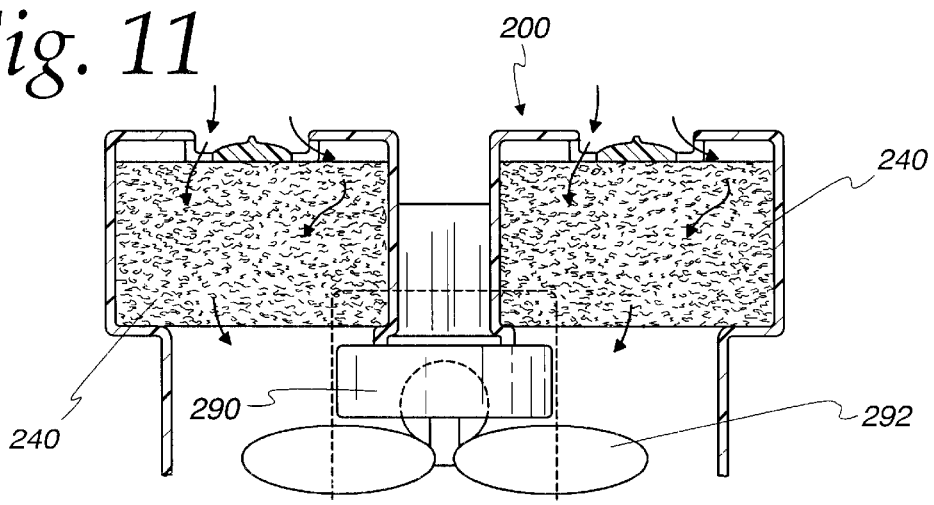
FIG. 11 is a cross-sectional view taken substantially along the line 11—11 of FIG. 10.

Referring now to the drawings for purposes of illustration, there is illustrated in FIG. 1 an isolation pod or apparatus 10 without having a flexible cover or housing wall 14 and in FIG. 2 is another embodiment of the invention having a transparent housing wall 14 and a flexible base 12 or drag bottom attached to the bottom of the housing wall 14. As will be explained in detail, the housing wall 14 or 14a is an airtight barrier wall to the passage of contaminants into or from the hollow interior of this isolation pod in which the patient is located. In the aforesaid pending application the drag bottom 12 was integrally attached to and was part of the housing wall 14. When used as a drag bottom, the base 12 is reinforced or made of a heavier material than the material of the housing wall; and a reinforced base is only or principally used as a drag bottom for dragging the pod 10 with a person in it in the field by the military. For many civilian uses and to reduce cost it is possible to provide an isolation apparatus 10 without the base attached thereto or to have a detachable drag bottom base 12. In another embodiment of the invention, shown in FIGS. 28 and 29, the isolation apparatus is in the form of a jacket or housing having a housing or barrier wall 14a which covers the upper torso and head and arms of an ambulatory patient. The transparent housing wall 14, which is shown in FIG. 1, and the housing wall 14a, which is shown in FIG. 28, are each made preferably of a flexible plastic material such as polyvinyl chloride which is transparent and has a thickness of 0.020 inch or less. In the aforesaid copending application, the thickness was described as being 0.020 inch whereas in the preferred and illustrated embodiments shown in this application, the wall thickness may be reduced to lower the cost of the plastic used. It will be appreciated that the barrier wall 14 could be made of opaque and of composite materials other than the plastic sheet material described herein. If the barrier wall is opaque, then transparent windows will be provided therein to view the patient.

Cost is a very important consideration in the sense that many civilian defense units or fire departments have extremely tight budgets and will not purchase very high priced isolation pod apparatus. On the other hand, if the price is sufficiently low, they will purchase and use such isolation pod apparatus rather than cleaning their vehicles and exposing themselves to infectious diseases or AIDS or the like. Also, for the military use and civilian uses against terrorist's attack, there will need to be stored large numbers on pallets or the like for transport to the scene. In the illustrated embodiment of the invention, there is a preferred head end which is to receive the head of the patient and a foot end which is to receive the feet of the patient and to this end it is preferred to provide a torso silhouette 13 at least at the head end to show a visible reminder to whomever is placing patients into the isolation pod the proper orientation of the patient within the pod. It should be remembered that the placing of patients into such isolation pods may be done under extreme duress, such as in battlefield conditions or terrorist attacks, and may not always be done by trained medical personnel but by others who are untrained and are pressed into duty because of an emergency. The illustrated silhouette 13 is merely a printed or painted silhouette of a patent's head and arms and torso at the top portion of the isolation pod on the lower clam shell half 30. The illustrated halves of the isolation pod open like a sleeping bag with three sides having a zipper 20 and the fourth long side without a zipper. On the other hand, the zipper could be extended around the fourth side to allow the halves to separate from one another; and later be joined by the zipper 20 at time of usage of the pod.

In order to prevent the patient from damaging the pod 10 after having been enclosed therein, it is preferred to provide a restraint, such as an upper belt 40 including a first half 44 and a second half 46 as well as a second lower belt 42 having a first half 48 and a second half 50, as shown in FIG. 3. These belts 40 and 42 are attached to reinforcing webs 31, 31a and 31b, which are described hereinafter.

Additionally, it is preferred that the base be provided with a cap drain 54 at one or both lower corners from which fluids may be drained from the interior of the pod when it is raised. Such fluids may be decontamination fluids put into the housing pod by the medical personnel or may be contaminated fluids generated by the patients themselves.

The housing wall 14 material of thin PVC is generally not sufficient in strength to support the patient without the base drag sheet. Where a drag sheet is not desired, a patient still may be transported by the use of selectively positioned reinforcing webs or straps (FIG. 3A) which are spaced along the pod and which are secured to the bottom layer of the bottom portion or half 30 of the clam shell. More specifically, at least three such webs, one web 31 at the shoulders, another web 31a at the hips and a third web 31b at the calves or feet, are supplied. Preferably, the webs have particular handholds therein, as best seen in FIG. 3A, to allow the patient, after he has been placed in the low clam shell half which is probably being laid out on the ground, to be lifted and placed onto a litter or on a fire truck gurney or the like. The drag sheet may be made of various materials and may be attached to the housing as by being integrally attached as in the aforesaid copending application or detachably attached thereto, as illustrated and described herein. The preferred attachment is made by simple pressure attachment devices such as a simple snap or clip 82 to provide a rapid connection which is readily understood by most people and which allows easy detachment of the base from the housing wall. Usually, the detachable drag bottom base is formed of a thicker material and can be of a different material, such as a nylon or a heavy, thicker PVC plastic material, if desired. Typically, the base, and particularly when it is a drag bottom, may have a plurality of rectangular hand holds or openings 56 into which a person's hands may be inserted and used to pick up the pod without having any supporting structure underneath it. The base may be provided as disclosed in the aforesaid application with grommets and tension members for engaging the grommets to allow overlapping of the base edges to be wrapped around a stretcher or litter to attach the pod securely to the stretcher for transport, as described in the aforesaid application. If desired, the isolation pod may have its own poles 83 (FIGS. 1 and 2) for attachment thereto. The isolation and treatment pod 10 can be used with various litter systems.

It is preferred that collapsible pod 10 have bendable, semi-rigid, arcuate stays or ribs 79 which act as support to keep the upper clam shell half of the housing wall 14 in a generally open expanded position about the patient prior to pressurization of the pod. The stays 79 are preferably plastic ribs which are heat sealed to the plastic wall 14 or can be inserted into a sleeve 80 in the form of a hollow strip or channel of plastic secured to the housing wall 14. The strips and stays may be formed, such as shown in the aforesaid copending application, where the sleeve forms a channel to receive the stay along the outside of the pod with an entryway formed in the bottom thereof to receive the stay. If desired, the upper clam shell half may have the stays inserted into these sleeves to erect the upper clam shell half in the field at the time of usage of the pod.

Figure 22:
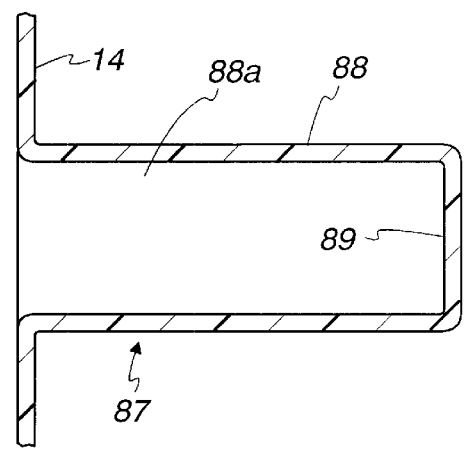
Figure 23:
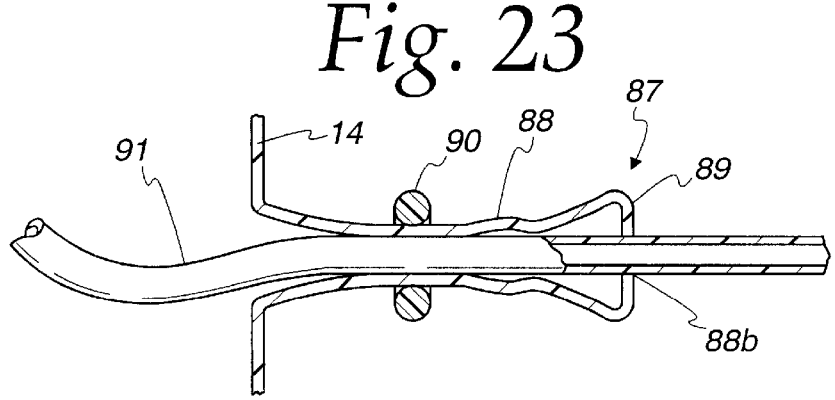
FIG. 23 is a cross-sectional view which illustrates a catheter tube inserted through the sleeve of FIG. 22 with the sleeve sealed about the catheter tube.

For the purpose of allowing the introduction of various lines into the interior of the apparatus for checking on the condition or providing fluids or medicines to the patient within the isolation pod, there is provided a plurality of small ports 87, such as those shown in FIGS. 1, 2 and shown in enlarged detail in FIGS. 22 and 23. As best seen in FIG. 22, the ports 87 are formed in the housing wall 14 and are normally provided with a tubular wall 88 having a closed end 89 and a hollow interior 88a with the closed end 89 either being clipped off or perforated as at 88b (FIG. 23) to allow a tube or line 91 to be inserted into the hollow interior and across the housing wall 14 in which the port opening is formed. The ports 87 are spaced along the barrier housing wall 14 and are used for EKG apparatus lines, oxygen lines, intravenous lines, defibrillator lines, suction lines or the like. Preferably these small ports 87 are positioned in the lower half 30 of the pod so that the lines or leads may stay connected to the patient whether the pod is in the open or closed position. The small ports may be closed with various port clips or such as the O-ring 90 shown in FIG. 23 encircling the sleeve as well as the intravenous tube 91. It is preferred that the port tubular wall 88 be encircled and closed against the tube or lead either by clips or other devices both prior to insertion of a intravenous tube or a lead and after the line or lead is therein, as shown in FIG. 23. These small ports 87 are usually positioned about the head area in the pod to allow suction lines or oxygen lines to be delivered to the head and about the chest area in the pod for intravenous lines and EKG lines. Other small ports may be provided where needed.

Figure 21:
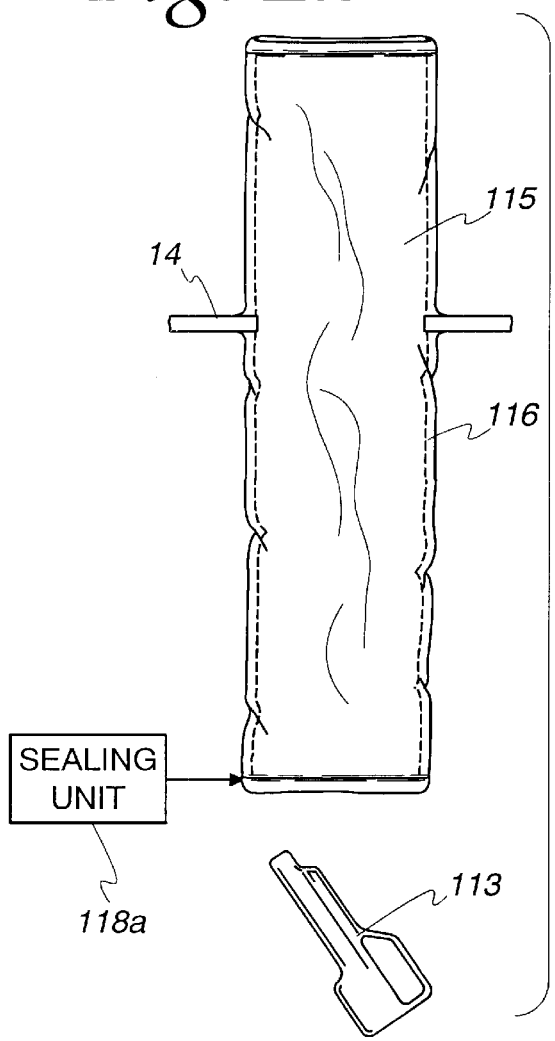
FIG. 21 is an elevational view which illustrates the sealing of the interior sleeve after the article has been passed through into the interior of the isolation pod.

In order to administer the intravenous materials to the patient in the pod to do an electrocardiogram, a blood pressure check, to clear the respiratory airway of the patient, deliver medicine, and to insert a ventilator tube for a respirator, it is important to provide one or more pass-through ports 110, such as shown in FIGS. 1, 2 and 3, 19 and 20, which includes in this instance an inner and outer sleeve formed on opposite sides of the sidewall 14. The pass-through 110 includes a pair of hollow sleeves 115 and 116 with the outer exterior sleeve 115 having a hollow interior 115b connected to and aligned with a hollow interior 116b in the lower interior sleeve 116 shown in FIGS. 16. An article 113, such as shown in FIGS. 19 and 21, may be passed through severed end 115a of the exterior sleeve 115 after it has been cut by a severing device 117 or the like which opens the hollow interior of the sleeve 115 to allow the insertion of the article therein which is then passed by the barrier wall 14 to the interior of the interior sleeve 116. As shown in FIG. 20, the opened upper end of the sleeve 115 is closed by a sealing unit 118 which could be a heat seal or could be a mechanical clip or tie. In any event, the outer sleeve 115 is sealed so that there is no ingress or egress of air and air borne contamination through the previously opened end 115a. Then using the glove ports, the lower end 116a of the interior sleeve 116 is severed as by a severing device 117a within the pod to provide the open end 116a through which the article may then be extracted (FIG. 21) from the interior of the lower sleeve 116. Pass-through ports 110 may be used to pass plastic bags containing objects through one at a time without breaching the containment of the pod.

It is desired to place one of the pass-through ports 110 near the head or the chest of the person where typically the medical personnel will be examining the head or chest of the patient, the patient's mouth and throat as well as the eyes of the patient and be using various instruments such as a stethoscope on the chest of the patient. To allow manipulation, examination, or access to the patient at the midsection or the torso as well as to the knees and the lower portion of the patient, the illustrated and preferred embodiment of the invention shown in FIG. 3 is provided with four sets of glove ports, generally designated as 150.

The number and location of the glove ports 150 may be varied from that illustrated in FIG. 3 where four pairs of glove ports are illustrated about the head, chest, waist and ankle locations of the patient. When looking down on a patient within the pod, each pair of glove ports will have one glove of the pair on the right side of the patient and the other of the glove pair on the left side of the patient. The respective right and left gloves 160 of each pair are aligned laterally opposite one another, as best seen in FIG. 3. Herein, there are a pair of head area, glove ports 150a and 150b, a pair of chest area, glove ports 150c and 150d, a pair of waist or stomach area, glove ports 150e and 150f, and a pair of ankle or feet area, glove ports 150g and 150h. Manifestly, the glove ports position can be changed from that illustrated and described herein.

Each of the glove ports 150 includes a glove 160, as best seen in FIG. 14, which may be a substantially ambidextrous, impermeable, chemical-resistance glove. Glove 160 is connected to a glove port sleeve 162 which extends to a glove port opening 164 (FIG. 14) formed in the barrier wall 14. The sleeve 162 is hollow and long to receive the wrist and lower portion of an arm of a medical person treating the patient. Herein the glove 60 is detachably connected to the sleeve 162 by a connection device 166 which includes a hollow, stiff, plastic sleeve portion 168 which is attached as by adhesive or otherwise to the distal end of sleeve 162. The glove has an upper end 160a which encircles and covers the lower end of the sleeve and is secured by a pair of O-rings 163 and 165. The O-rings clamp the upper end 160a of the glove to a lower end of the sleeve 168 in an airtight manner. In this manner, the rigid hollow sleeve 168 and the O-rings 165 and 163 serve to provide a detachable interconnection between the gloves and the sleeve 162.

A suitable glove cover or closure 166 is provided to close the opening 164 in the barrier wall 14 leading to the hollow interior in the sleeve 162 and the glove 160 until it is desired to have the caregiver insert his hand or arm into the glove port 150.

Figure 24:
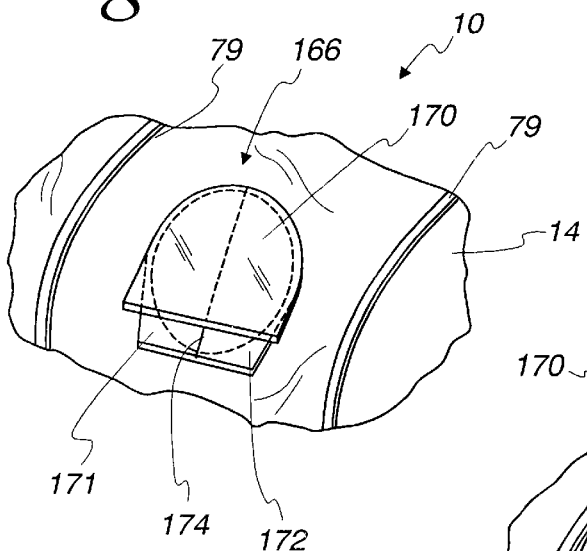
FIG. 24 is a perspective view which illustrates a cover for the pass-through port.
Figure 25:
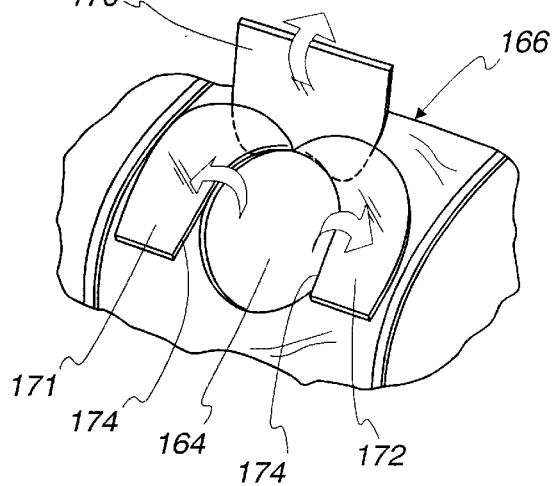
FIG. 25 is a perspective view showing covers being opened to allow access to the glove port.
Figure 26:
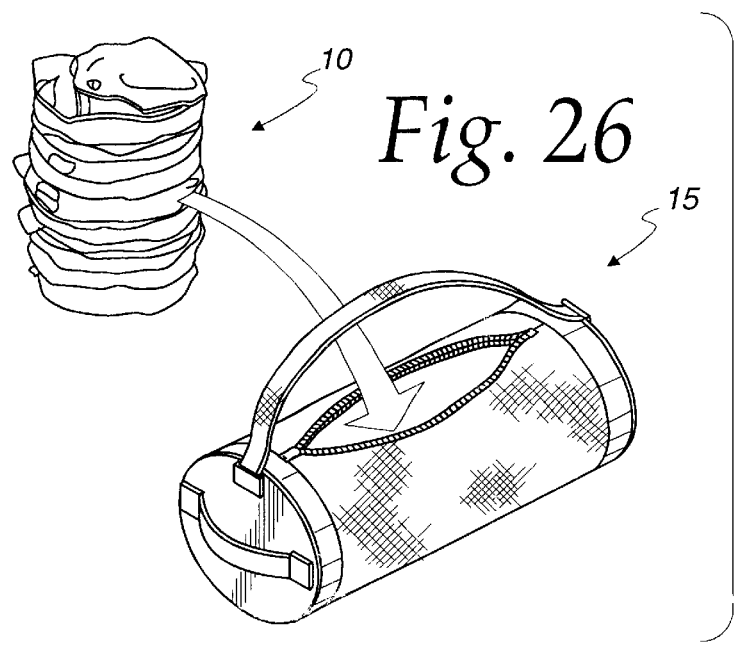
FIG. 26 is a perspective view which illustrates the collapsing of the isolation pod of FIGS. 1 and 2 and the insertion thereof into a carrier.

The illustrated glove port cover 166 may take various forms and was described in the aforesaid copending application as including an airtight zipper type closure. Herein the glove port cover 166 is preferably, as best seen in FIGS. 24 and 25, provided with three cover flaps including a pair of slide flaps 171 and 172 formed of the same plastic material and attached at their upper ends to the sidewall 14. An overhead and outer central flap 170 overlies the other two flaps 171 and 172 and is secured to the barrier sidewall 14. The flaps drape downwardly by gravity to cover one another and to form a seal or cover, such as shown in FIG. 24, wherein the overlying central flap 170 is seen overlying the abutted, inner edges 174 of the respective flaps 171 and 172 to cover and seal the glove port opening 164 against filling with decontamination fluids, which will typically be a decontamination liquid being used to wash down the exterior wall 14 of the pod 10. Also, the glove port cover prevents material from falling into the open glove port arm during transportation or the like of the patient or storage of the pod. Thus, it will be seen that the glove port may be used to manipulate the patient within the pod without breaking the airtight barrier and releasing contaminants from the pod 10 into the environment or allowing contaminants from the environment to reach into the interior of the pod and to the patient.

As stated previously, a plurality of drain ports 94 are provided at the lower outer foot end of the pod 10 through which liquids may be drained via gravity when tilting the pod with the patient inside the pod to cause the flow to the lower outer ends of the pod. Herein the drain ports may be normally closed by threaded gaps which may be unscrewed threaded nipples in the barrier wall which are desired to allow drainage. After drainage the drain ports 94 and 94a may be closed by the threaded caps.

In accordance with an important aspect of the invention, the patient is provided with an air flow of a predetermined rate such as 4–6 cm cfm at a pressure of 4 inches of water to prevent a buildup of carbon dioxide about the patient's head and to remove moisture that would fog the interior of the plastic housing wall 14, thereby interfering with the patient's view and also interfering with the view of the medical personnel observing the patient within the pod. As will be explained in detail, it is preferred that the tightness of the housing wall 14 and the dynamics of the air flow are such that the air leakage is kept within a predetermined range. The pod will meet the desired air tightness standard that not more than 20% of the air leaking from the housing pod over a five-minute period after the stopping of the air flow into the housing pod. The pressurized air flow also expands the plastic housing wall in addition to the ribs 79 which are expanding the housing wall to keep it from touching the patient and particularly from touching any wounds the patient may have. The apparatus includes an airtight closure or zipper device, such as that made by YKK of Japan. Unidirectional air flow valves at the air inlet and exhaust ports prevent air outflow through either of these ports.

In accordance with another important aspect, it is preferred that the air be purified or filtered prior to flow into the containment pod 10 and also prior to being exhausted from the pod into the ambient atmosphere. In crisis situations, the medical personnel may be unsure or make a mistake as to which air is to be purified, that is, whether the ambient air is contaminated and needs to be purified or the atmosphere within the containment device is contaminated and needs to be purified. To this end there is provided an air purifier device 200 (FIGS. 1 and 2) which blows air which has been filtered by passing through a Class 1 type of filter and this filtered air is delivered through a hose 201 into the interior of the housing through a ventilation port 203 (FIG. 3) with the air entering the pod 10 generally at or adjacent the head of the patient to sweep across the patient's head so that the patient feels less claustrophobic. A good air sweep is provided to assist the patient in breathing. At the foot of the pod, air is extracted through a ventilation port 205 connected to a hose 207 leading to an exhaust purification or filtering device 210 which purifies and filters the air leaving the isolation pod 10.

Referring now in greater detail to the exhaust purifying device 210, it is illustrated in greater detail in FIGS. 4–8 and comprises a filter housing 220 of rigid plastic which provides a hollow interior, large chamber 222 of a large volume relative to the hose 207 and the air passages within a one way air valve 224 at the inlet to the large chamber 222. The large chamber is used because it does not restrict the flow of air or constrain the air so that the desired throughput and low back pressure is maintained despite a restricted flow of air across the one way air valve 224 and the filters 235 and 236 which are located in a hollow bore in a cylindrical wall 226 of the filter housing 220. The outer end of the hose 207 is attached to the cylindrical housing wall 207.

As best seen in FIG. 5, the air flows in the direction of the arrows past the one way valve 224 into the large hollow interior chamber 222 and then the air splits and flows sideways through side exits or outlets 227 and 228 of the housing and then through the attached air filters 235 and 236. Each of the filter devices 235 and 236 has an interior filter material 240 which may include carbon and other materials needed to purify the air by filtering out contaminants or by a chemical reaction. The filtered air exits from the exhaust port screens 241 at smaller diameter, outlet ends 242 of the respective filter devices 235 and 236. The illustrated filter devices are commercially available filter devices made by several safety product companies and they are shown being used in the reverse manner because they are usually used with the inlet air flowing through the small diameter ends 242 and with the air exiting the large diameter housing end 232.

The pair of exhaust air filters 235 and 236 are each connected to the filter housing 220 by a soft, flexible member or connector 239 that has a large diameter sleeve 241 which is telescoped over the respective rigid cylindrical walls 235a and 236a of the respective filters 235 and 236. The intimate contact between the sleeve 241 and these cylindrical walls 235a and 236a prevents air leakage or any contaminant leakage and physically joins the filters to these outer, large diameter sleeves 241 of the respective connectors 239. The flexible sleeve 241 fits over the filter cannister and it has integrally molded small diameter ends 250 which fit over the exit ports 227 and 228 on the exit filter box housing 220. That is, each of the connectors has a small diameter sleeve 250 that telescopes over the small diameter, cylindrical outlets 227 and 228 of the rigid plastic, filter housing 220. These soft, small diameter sleeves 250 are telescoped over the outlets 227 and 228. Suitable hose clamps 254 encircle the soft pliable plastic sleeves 250 and force them tightly against the respective rigid housing outlets 227 and 228 to prevent air or contaminant leakage.

Referring now to the one way valve 224 which allows air flow in only one direction which is in the exit direction for the devices shown in FIGS. 4–8, the illustrated one way valve is formed of plastic and comprises a hard rigid plastic housing portion or body with a central cone 262 and six spider or arms 264 which extend outwardly from an inner ring 262a at the base of the pin 262. At the outer ends of the spiders is a ring 267 of hard plastic joining the ends of the spider arms 264. Secured to the plastic ring 267 are six diaphragm leaves or flaps 266 of soft, bendable plastic. Each of the leaves 266 has its radially outer end 266a secured to the outer rigid ring 267 with the interior small portions 266b of the leaves 266 being flexible and pliable to be flexed outwardly by the air flow and the pressure of the outflowing air flowing in the direction of the arrows through an opening 268, as best seen in FIG. 8. On the other hand, when the air flow is in the opposite direction, the leaves and ends 266b thereof are pushed downwardly with their inner ends 266b resting against the ring 262a and there is no bending past the ring in the opposite direction thereby closing off any air flow past the leaves 266. As best seen in FIG. 6, it is preferred to make the leaves 266 with a generally curved shape. Manifestly, the valve described and illustrated herein is one embodiment of the invention and other checked valves or other valves may be used from that illustrated and described herein.

Figure 12:
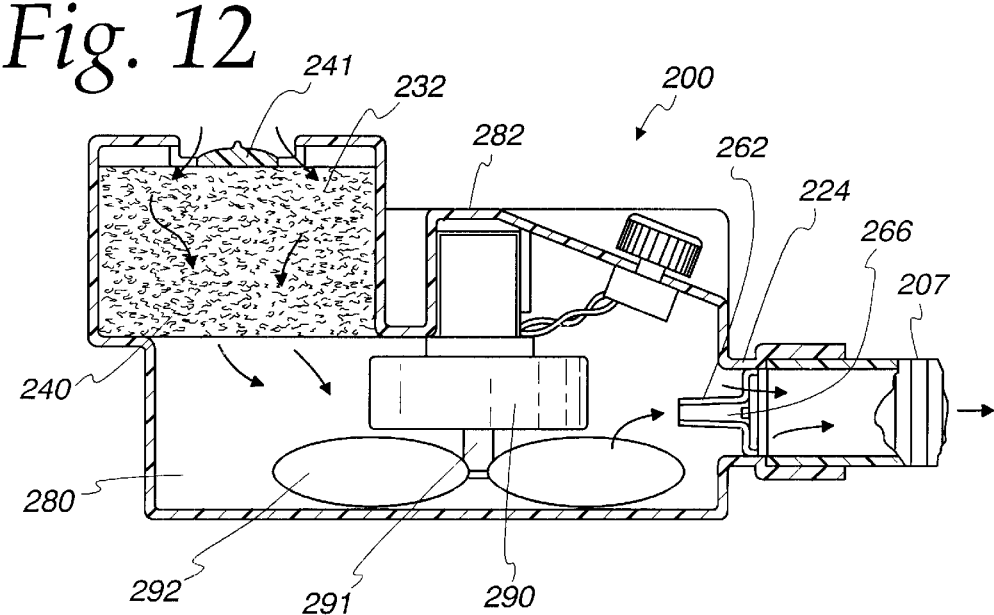
FIG. 12 is a cross-sectional view taken substantially along the line 12—12 of FIG. 10.
Figure 13:
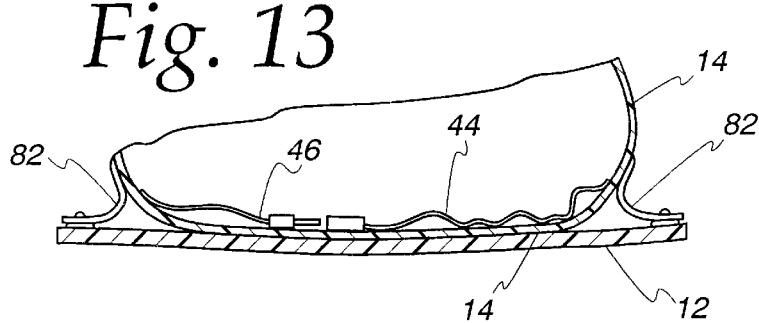
FIG. 13 is a cross-sectional view which illustrates restraint straps within the isolation pod.
Figure 15:
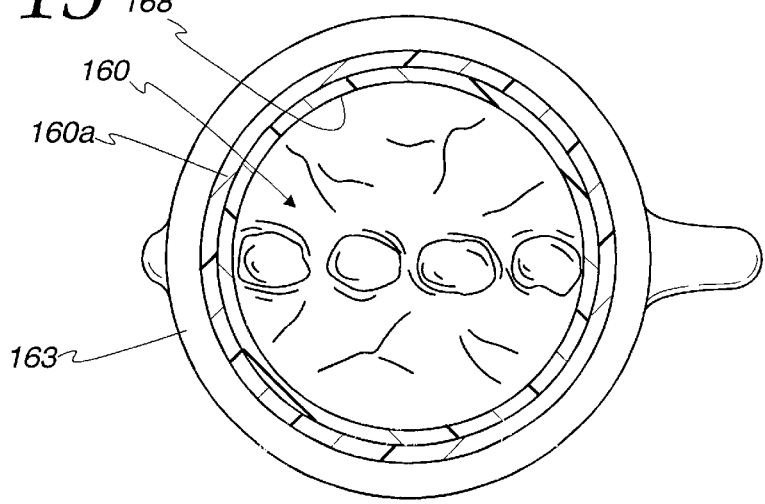
FIG. 15 is a cross-sectional view taken substantially along the line 15—15 of FIG. 14.

The same one way air valve 224 is also used with the air inlet purifier device 200 which is shown in FIGS. 9–12. As best seen in FIG. 12, the valve 224 has its pin 262 within the interior hollow chamber 280 of a rigid filter housing 282 with the air flow bending the valve leaves 266 to allow air flow in the direction of the arrows shown in FIG. 12. Reverse flow is not permitted by the valve 224. The illustrated inlet air purifier and blower device 200 includes a blower motor 290 which has a shaft 291 for rotating fan blades 292 to drive the air in the direction of the arrows past the one way valve and into the hose 201 which is connected to the ventilation port at the head end of the pod 10. The air purifier device 200 has a pair of filter devices 232 (FIG. 10) which are identical to the air filter devices 235 and 236 used at the exhaust end and previously described. The only difference is that the direction of the air is opposite with the air flow coming through the small diameter portions 241 and then flowing into the filter material 240 and through this filter material to exit the large diameter end of the filter into the interior hollow chamber 280 in which is housed the blower for driving the air. As shown in FIGS. 9–12, the preferred housing 280 is generally triangular in shape with the pair of filter units 232 being upright cylinders at one end and with the hose 201 being connected by a threaded hose coupling 295 (FIG. 10) to the housing adjacent a narrow outlet end 296.

In the ambulatory embodiment of the invention, as illustrated in FIGS. 28–31, the patient is still able to walk and the medical personnel are willing to allow the patient to walk while being within the isolation apparatus 10a. In this instance, the isolation apparatus comprises a jacket type of barrier wall 14a that has a hood or head covering 300 that encloses the head of the patient and also has attached airtight gloves 302. Preferably, an airtight closure 304 in the form of an airtight zipper 306 is provided in the back of jacket wall 14a with the zipper extending from the top of the hood down to the lower end of the jacket which is at the waist of the patient. It is preferred to provide the zipper at the back so that the patient is not able to open the zipper by himself.

Herein, the jacket wall 14a is made of the same thin, flexible plastic such as a polyvinyl chloride in the range of less than 0.020 inch thick or less. When purified air is blown into the hollow interior 312 in the jacket wall 14a through an air inlet hose 314 the jacket wall expands to keep most of the jacket off of the patient's body and any wounds the patient may have. Also, the expansion of the hood 300 by the air pressure of the confined air allows the patient to see more clearly with the plastic wall 14a being spaced from the patient's face. Herein, the inlet purified air is provided by the inlet air blower unit 200 of FIGS. 9–12 and the exhaust air leaving through hose 318 is directed into the air purifier unit 210 (FIGS. 4–6), each of which air purifier units have been described above and hence need not be described again in detail. The preferred air flow is 4–6 cfm at a pressure of about 4 inches of water, as described above, to prevent carbon dioxide build-up to excessive levels and to keep the plastic housing from fogging and interfering with the patient's view.

To keep the enclosed chamber 312 with the jacket isolation pod airtight, a jacket end closure 325 is used at the patient's waist to prevent ingress or egress of contaminants. To this end, the jacket end closure 325 comprises an adhesive tape 327 that adheres to the skin 329 of the patient at the patient's waist. As illustrated, it is preferred to have the adhesive tape closure 325 encircle the patient's waist and be adhered in airtight contact with the skin at the patient's waist. The adhesive tape closure 325 is attached to a lower end 330 of the jacket isolation pod along an interior edge thereof. Herein, the attachment is by means of adhesive layer 332 (FIGS. 30 and 31) which is on one side of a carrier layer or substrate 334. The adhesive layer 327, which adheres to the patient's skin, is on the other side of the carrier substrate 334. A protective, peelable inner strip or layer 336 is adhered to the patient adhesive layer 327 until the time of usage when the peelable strip 336 is removed exposing the adhesive layer 327 for attachment to the patient's skin. Preferably, the adhesive tape 327 comprises a series of thin, flexible, pliable layers 336, 327, 334 and 332.

Also, the jacket closure 327 preferably includes a drawstring 340 encircling the patient's waist to draw the lower end 330 of the jacket plastic wall 14a against the patient's waist and to hold the jacket wall physically against the patient's waist and to resist forces that would tend to pull free the adhesive layer 327 from the patient's skin during the patient's treatment or ambulation. The adhesive layer should adhere sufficiently that it does not come loose during usage of the jacket isolation pod; but yet, can be stripped from the patient's skin without tearing the patient's skin and causing a high degree of pain.

For storage, the jacket isolation pod 10a may be collapsed and it is preferred that the air inlet and air exhaust purifier units 200 and 210 are separated from jacket wall 14a when the jacket barrier wall 14a is collapsed. It is preferred to have a pair of threaded nipples or connectors 350 (FIGS. 27 and 28) mounted on the jacket barrier wall 14a at the patient's shoulder or chest area for connection to the respective air inlet hose 314 and air outlet hose 316. Each of these hoses has a rotatable male, threaded connector 352 on the ends of the hoses for threading onto the threaded nipples 350 when the isolation pod 10a is to be used.

From the foregoing, it will be seen that there has been provided an inexpensive isolation pod that is readily transportable such as on a litter in FIGS. 1 and 2 or by ambulatory patient in FIGS. 28 and 29. The isolation pod is useable for evacuation of battlefield casualties from a biological or chemical attack in that it is readily used with litters and litter poles. While not shown in the ambulatory pod 10a in FIGS. 28 and 29, the barrier wall 14 or 14a may be provided with glove ports, pass-through ports and other small ports for IV tubes, instrument leads, etc. The isolation pods 10 and 10a require attached purifier or filtering units that are portable and are relatively small and light in weight. These isolation pods are inexpensive in that they are made with thin, flexible materials and provide soft walls that are collapsible to be stored in a relatively small volume. While the barrier walls 14 and 14a have been described as being made of plastic in the illustrated embodiments of the invention, the soft barrier walls 14 or 14a may be made of composite or laminated materials having layers of different materials and permeabilities. It will be appreciated that barrier wall 14 or 14a could be made of opaque material with transparent plastic windows therein rather than being entirely transparent plastic, as in the illustrated embodiments described herein. While the stays used herein are preassembled to keep the upper covering portion spaced from the patient, the stay system for this upper covering portion could be assembled in the field at the time of usage of the isolation pod. A full length zipper allows easy entry and exit for the patient.

The present invention may also be incorporated into wraps for civilian use in scenarios involving a limited number of pods for contaminated patients such as might be present in a chemical incident or for persons who would need to have medical attention administered through the wrap. In addition, suits may be provided including a power respirator hood that creates negative pressure within the hood and including rib or other supports for supporting the suit in particular the hood away from the person when the suit is being run in a negative pressure mode to prevent the suit from collapsing around the person.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A collapsible, protective containment device for isolating a patient in a controlled environment for use without a litter and for attachment to a litter for transport of the patient while therein, the device comprising:

a flexible, tubular containment wall expandable from a collapsed, folded state to define an interior region for receiving at least a portion of a patient therein and providing an impermeable barrier wall about the portion of the patient therein;

at least a portion of the containment wall being clear to allow observation of the patient and to allow the patient to see through the clear containment wall portion;

a closure device for closing the flexible containment wall about the patient to provide a substantially airtight interior region at least about the head of the patient;

an air ventilation device including a filter for filtering air being transmitted between the substantially airtight interior region and the ambient atmosphere;

the tubular containment wall having a flexible top wall portion and a flexible, bottom wall portion each foldable into a collapsed form to a reduced, overall length for storage; and reinforcement straps spaced from each other along the flexible bottom wall to allow carrying of the patient without tearing the bottom wall.

2. A portable collapsible containment device in accordance with claim 1 wherein the air filtration device filters the air being exhaled by the patient and flowing from the interior region to the ambient atmosphere to protect against transmission of an infectious disease from the patient; and a one-way airflow device to prevent an out-flow of air through an air inlet from the interior region.

3. A collapsible, protective containment device in accordance with claim 1 wherein the air filtration device filters inlet air flowing into the interior region to protect the patient from foreign material in the ambient atmosphere; and a one-way airflow device to prevent a reverse flow of air from the interior region outwardly from the interior region through an air inlet port.

4. A portable, collapsible, containment device in accordance with claim 1 where the air filtration device comprises:

a filter for filtering the entry air flowing into the interior region; and a filter for filtering the exhaust air leaving the interior region to provide clean air to the patient and clean exhaust air being discharged into the ambient atmosphere.

5. A collapsible containment device in accordance with claim 1 wherein the flexible containment wall defines a torso silhouette for assisting in proper patient orientation within the containment device.

6. A collapsible containment device in accordance with claim 5 wherein the cinch comprises:

a double-sided tape adhered to the containment wall of the jacket portion and having the adhesive layer thereon for adhering to the patient.

7. A collapsible containment device in accordance with claim 1 wherein the collapsible containment wall is generally in the shape of a sleeping bag; and the closure device comprises a substantially airtight zipper extending lengthwise and about both ends of the patient to allow ease of placing a patient in the device and for forming a substantially airtight interior region about the patient.

8. A collapsible containment device in accordance with claim 1 wherein the flexible containment wall comprises a thin, flammable plastic material that is inexpensive enough to be burned to dispose of the containment device if it is thought to be contaminated.

9. A collapsible containment device in accordance with claim 1 wherein the air filtration device comprises an air blowing device to provide airflow rate to inflate the collapsible, flexible containment wall to keep it at least partially off the patient's body.

10. A collapsible containment device in accordance with claim 1 comprising supports associated with the containment wall to hold the containment wall away from the patient.

11. A collapsible containment device in accordance with claim 10 wherein the supports comprise:

spaced ribs having arcuate portions to hold an upper side of the containment wall spaced from a bottom portion on which the patient lays.

12. A collapsible containment device in accordance with claim 11 wherein the spaced ribs are spaced farther apart when the containment device is in use and are brought closer together as the containment device is collapsed in an accordion fashion.

13. A collapsible containment device in accordance with claim 1 comprising at least one selectively openable port on the containment wall for receiving an IV tube or electrical leads.

14. A collapsible containment device in accordance with claim 13 wherein the selectively openable port comprises a plastic sleeve having a closed end that can be opened to admit an IV tube or electrical leads.

15. A collapsible containment device in accordance with claim 14 wherein a plurality of the plastic sleeves are provided in the containment wall on each side of the patient.

16. A collapsible containment device in accordance with claim 1 wherein the air filtration device provides a flow rate in the range of 4 to 6 cfm to prevent an undesirable amount of carbon dioxide accumulation in the interior region.

17. A collapsible containment device in accordance with claim 1 wherein the air filtration device provides an air pressure inside the interior region of at least about 4 inches of water.

18. A collapsible containment device in accordance with claim 17 wherein the pressure is maintained in the interior region with a loss of pressure being less than 20 percent during a five-minute period.

19. A collapsible containment device in accordance with claim 1 comprising:

at least one hose connector fixed to the container wall having an air chamber therein and a portion for connection of a hose and for providing directional airflow through the interior region.

20. A collapsible containment device in accordance with claim 15 comprising:

at least one exit filter attachment associated with the housing connector to connect an internal airflow passageway within the housing connector to an exit air filter to have exit air flow in the correct direction for filtering.

21. A collapsible containment device in accordance with claim 20 wherein the filter attachment comprises:

a flexible cap for encircling an end of the exit air filter and for providing an airtight seal therewith.

22. A collapsible containment device in accordance with claim 21 wherein the exit filter attachment comprises:

an exit port housing having a one-way valve therein a pair of exit ports;

a pair of flexible caps attached to exit ports for the exit port housing; and a pair of filters attached to the flexible caps.

23. A collapsible containment device in accordance with claim 8 wherein the hose connector comprises:

an outer, rigid housing body having an interior chamber;

a check valve within the housing body's interior chamber to cause unidirectional airflow; and a hose connection on the housing body for connection to the interior region within the containment device.

24. A collapsible containment device in accordance with claim 1 comprising:

a check valve associated with a filtration device to provide an unidirectional flow of air with respect to the interior region.

25. A collapsible containment device in accordance with claim 1 comprising:

at least one glove port near the patient's head;

at least one glove port near the patient's sternum; and at least one glove port near the patient's knees.

26. A collapsible containment device in accordance with claim 1 comprising:

at least one glove port in the containment wall having an opening in the containment wall and a long sleeve for providing access into the interior region to manipulate the patient or items in the interior region; and a glove port cover covering the opening to allow decontamination of the exterior without filling the sleeve with a decontamination fluid.

27. A collapsible containment device in accordance with claim 26 wherein the glove port cover comprises overlapping pieces of plastic defining an iris configuration.

28. A collapsible containment device in accordance with claim 1 comprising a pass-through port in the containment wall for exchange of items from the exterior of the containment device into the interior region.

29. A collapsible containment device in accordance with claim 28 wherein the pass-through port comprises:
   an inner sleeve having a first hollow passageway and a closed, severable distal end projecting into the interior region; and
   an outer sleeve having a second hollow passageway communicating with the first passageway and a closed severable distal end located outwardly of the containment wall.

30. A collapsible containment device in accordance with claim 28 comprising:
   a glove port located adjacent the pass-through port so that items being passed into the interior region through the pass-through port may be handled by a hand in the adjacent glove port.

31. A collapsible containment device in accordance with claim 1 comprising:
   a glove;
   a connecting portion on the containment wall at the glove port; and
   an O-ring for securing the glove to the connecting portion and to provide a substantially airtight connection therebetween.

32. A collapsible containment device in accordance with claim 13 comprising:
   a long sleeve portion on the glove to allow the insertion of an arm through the glove port and into the interior region to treat the patient.

33. A collapsible containment device in accordance with claim 1 wherein the flexible containment wall has an upper portion and a lower portion joined together to define the shape of clam shell halves; and
   a substantially airtight zipper for joining together the clam shell halves to enclose the patient in the containment device.

34. A collapsible, protective containment device for isolating a patient in a controlled environment and for transport of the patient while therein, the device comprising:
   a flexible containment wall expandable from a collapsed state to define an interior region for receiving at least a portion of a patient therein and providing an impermeable barrier wall about the portion of the patient therein;
   at least a portion of the containment wall being clear to allow observation of the patient and to allow the patient to see through the clear containment wall portion;
   a closure device for closing the flexible containment wall about the patient to provide a substantially airtight interior region at least about the head of the patient;
   an air ventilation device including a filter for filtering air being transmitted between the substantially airtight interior region and the ambient atmosphere;
   the flexible containment wall having an upper portion and a lower portion joined together to define the shape of clam shell halves;
   a substantially airtight zipper for joining together the clam shell halves to enclose the patient in the containment device; and
   a drag bottom on the lower clam shell half of a heavier and stronger material than the material of the upper clam shell half to allow dragging of the containment device and the patient therein along the ground.

35. A collapsible, protective containment device for isolating a patient in a controlled environment and for transport of the patient while therein, the device comprising:
   a flexible containment wall expandable from a collapsed state to define an interior region for receiving at least a portion of a patient therein and providing an impermeable barrier wall about the portion of the patient therein;
   at least a portion of the containment wall being clear to allow observation of the patient and to allow the patient to see through the clear containment wall portion;
   a closure device for closing the flexible containment wall about the patient to provide a substantially airtight interior region at least about the head of the patient;
   an air ventilation device including a filter for filtering air being transmitted between the substantially airtight interior region and the ambient atmosphere; and
   a detachable drag bottom having attachable portions thereon for assisting in attaching the drag bottom to the containment device when it is desired to add a drag bottom to the containment device.

36. A collapsible containment device in accordance with claim 35 comprising:
   detachable clips for attaching and detaching the drag bottom to the containment device.

37. A collapsible containment device in accordance with claim 1 comprising:
   an extension portion on a foot portion of the containment device; and
   an exhaust filtration device mounted on the extension portion for transport of the exhaust filtration device with the patient in the containment device.

38. A collapsible containment device in accordance with claim 37 comprising:
   a detachable connection between the exhaust filtration device and the of the exhaust filtration device on the extension portion to allow attachment and removal of the exhaust filtration device from the containment device.

39. A collapsible, protective containment device for isolating a patient in a controlled environment and for transport of the patient while therein, the device comprising:
   a flexible containment wall expandable from a collapsed state to define an interior region for receiving at least a portion of a patient therein and providing an impermeable barrier wall about the portion of the patient therein;
   at least a portion of the containment wall being clear to allow observation of the patient and to allow the patient to see through the clear containment wall portion;
   a closure device for closing the flexible containment wall about the patient to provide a substantially airtight interior region at least about the head of the patient;
   an air ventilation device including a filter for filtering air being transmitted between the substantially airtight interior region and the ambient atmosphere;
   an extension portion on a foot portion of the containment device; and
   an exhaust filtration device mounted on the extension portion for transport of the exhaust filtration device with the patient in the containment device;
   a drag bottom on the containment device for dragging along the ground; and the extension portion being an extension on the drag bottom projecting beyond the containment wall.

40. A collapsible, protective containment device for isolating a patient in a controlled environment and for transport of the patient while therein, the device comprising:
   a flexible containment wall expandable from a collapsed state to define an interior region for receiving at least a portion of a patient therein and providing an impermeable barrier wall about the portion of the patient therein;
   at least a portion of the containment wall being clear to allow observation of the patient and to allow the patient to see through the clear containment wall portion;
   a closure device for closing the flexible containment wall about the patient to provide a substantially airtight interior region at least about the head of the patient;
   an air ventilation device including a filter for filtering air being transmitted between the substantially airtight interior region and the ambient atmosphere; and
   a fluid drain at a patient's foot portion of the interior region on a side corner of the foot portion.

41. A disposable, collapsible, protective containment device for isolating a patient in a controlled environment and for transport of the patient while therein, the device comprising:
   a flexible thin plastic enclosure sheet expandable from a collapsed state having a reduced overall length for the containment device to an expanded state to define a tubular containment device for encircling the patient and to cover a patient being down within the tubular containment device, an interior region for receiving at least a portion of a patient therein and providing an impermeable barrier wall about the patient;
   the thin plastic enclosure sheet having a clear portion to allow observation of the patient and to allow the patient to see through the clear sheet;
   a closure device for closing the flexible sheet about the patient to provide a substantially airtight interior region at least about the head of the patient;
   an air inlet port on the flexible enclosure sheet for connection to a portable air handling system for flowing air into the interior region;
   an air outlet port on the flexible closure sheet for connection to a portable, air handling system; and
   the enclosure sheet being made of plastic 20 mil. or less thick to provide a low-cost disposable containment device for being disposed by burning after contamination.

42. A collapsible, protective containment device for isolating a patient in a controlled environment and for transport of the patient while therein, the device comprising:
   a flexible containment wall expandable from a collapsed state to define an interior region for receiving at least a portion of a patient therein and providing an impermeable barrier wall about the patient;
   at least a portion of the containment wall being clear to allow observation of the patient and to allow the patient to see through the clear containment wall portion;
   a closure device for closing the flexible containment wall about the patient to provide a substantially airtight interior region at least about the head of the patient;
   semi-rigid support ribs connected to the containment wall to hold the containment wall spaced from at least the upper portion of the patient within the protective containment device when a negative air pressure is maintained inside the interior region to prevent air from flowing outwardly from a contaminated patient within the interior region;
   an air flow device for removing air from the substantially air tight region and creating a negative air pressure within the containment device; and
   an air ventilation device including a filter for filtering air and through which air is transmitted from the substantially airtight interior region to the ambient atmosphere.

43. A collapsible, protective containment device for isolating an ambulatory patient in a controlled environment and for transport of the patient while therein, the device comprising:
   a jacket having sleeves, a torso and a head covering portion;
   the jacket being made of thin plastic sheet expandable from a collapsed state to define an interior region inside the jacket and providing an impermeable barrier wall about a portion of the ambulatory patient as the patient walks;
   at least the head covering portion of the plastic sheet being clear to allow observation of the patient and to allow the patient to see forming an air impermeable barrier about the upper portion of the ambulatory patient;
   a closure device for closing the jacket about the patient to provide a substantially airtight interior region at least about the head of the patient; and
   an ambulatory air ventilation device carried by the ambulatory patient for supplying air to the covering portion of the jacket and having a filter for filtering air being transmitted between the substantially airtight interior region and the ambient atmosphere.

44. A collapsible, protective containment device for isolating a patient in a controlled environment and for transport of the patient while therein, the device comprising:
   a flexible containment sheet expandable from a collapsed state to define an interior region for receiving at least a portion of a patient therein and providing a substantially air-impermeable barrier about the patient;
   a closure device for closing the flexible containment sheet about the patient to provide a substantially airtight interior region at least about the head of the patient; and
   an air ventilation device including a filter for filtering air and for providing an air-flow rate and an air-flow path to prevent an undesirable buildup of carbon dioxide in the interior region while transmitting air between the interior region and the ambient atmosphere.

45. A protective containment device for battlefield evacuation and treatment of a patient undergoing chemical or biological attack, the containment device comprising:
   a soft walled housing having a lower portion and an upper portion;
   a bottom wall on the lower portion adapted to receive a patient to lie thereon;
   an upper wall on the upper portion having transparent portions therein to allow viewing of the patient;
   stays associated with the upper portion to keep the upper wall spaced from the patient at least for a substantial portion of the patient's body;
   an air ventilation unit for providing filtered air to the patient within the soft walled housing;
   glove ports providing a safe access to the patient; and
   attachments for interconnecting the soft wall housing to a litter system for transport of the patient.

46. A protective containment device in accordance with claim 45 comprising:
an elongated zipper extending about at least three sides of the upper and lower housing portions to join the housing portions together.

47. A protective containment device for battlefield evacuation and treatment of a patient undergoing chemical or biological attack, the containment device comprising:
a soft walled housing having a lower portion and an upper portion;
a bottom wall on the lower portion adapted to receive a patient to lie thereon;
an upper wall on the upper portion having transparent portions therein to allow viewing of the patient;
stays associated with the upper portion to keep the upper wall spaced from the patient at least for a substantial portion of the patient's body;
an air ventilation unit for providing filtered air to the patient within the soft walled housing;
glove ports providing a safe access to the patient; and
attachments for interconnecting the soft wall housing to a litter system for transport of the patient;
an elongated zipper extending about at least three sides of the upper and lower housing portions to join the housing portions together; and
pass-through ports in the housing to allow food or medicine to be passed to the patient; and
patient restraints within the housing.

48. A collapsible, protective containment device for isolating a patient in a controlled environment and for transport of the patient while therein, the device comprising:
a flexible containment wall expandable from a collapsed state to define an interior region for receiving at least a portion of a patient therein and providing an impermeable barrier wall about the portion of the patient therein;
at least a portion of the containment wall being clear to allow observation of the patient and to allow the patient to see through the clear containment wall portion;
a closure device for closing the flexible containment wall about the patient to provide a substantially airtight interior region;
a first inlet air filtration device for filtering the inlet air flowing into the interior region to protect the patient from foreign materials in the ambient atmosphere;
a second air exhaust, filtration device for filtering the air being exhaled by the patient and flowing from the interior region to the ambient atmosphere to protect against transmission of an infectious disease from the patient; and
the first air filtration device and the second air filtration devices each having substantially identical filter units with the filter unit of the exhaust filtration device being reversed in position relative to the position of the filtration device for the air inlet device.

49. A collapsible, protective containment device for isolating a patient in a controlled environment and for transport of the patient while therein, the device comprising:
a flexible containment wall expandable from a collapsed state to define an interior region for receiving at least a portion of a patient therein and providing an impermeable barrier wall about the portion of the patient therein;
at least a portion of the containment wall being clear to allow observation of the patient and to allow the patient to see through the clear containment wall portion;
a closure device for closing the flexible containment wall about the patient to provide a substantially airtight interior region;
an inlet air filtration device for filtering the air flowing into the interior region to protect the patient from foreign materials in the ambient atmosphere;
the head and foot portions of the protective containment device being substantially similar in appearance; and
a silhouette representing a person on the containment wall to assist in properly orienting the patient to have the patient's head located properly at the head portion of the protective containment device.

50. A collapsible, protective containment device, useable without a litter, for isolating a patient in a controlled environment and for transport of the patient while therein, the device comprising:
a flexible containment wall expandable from a collapsed state to define an interior region for receiving at least a portion of a patient therein and providing an impermeable barrier wall about the portion of the patient therein;
at least a portion of the containment wall being clear to allow observation of the patient and to allow the patient to see through the clear containment wall portion;
a closure device for closing the flexible containment wall about the patient to provide a substantially airtight interior region;
a first inlet air filtration connection on the containment wall for connection to an air filtration device that is not attached to the connection when the containment wall is in the collapsed state and that is stored separately from the protective containment device;
the containment wall being unsupported by a litter;
a second air outlet connection on the containment wall for connection to a air filtration device that is not attached to the second air outlet connection when the containment wall is in the collapsed state and that is stored separately from the protective containment device; and
the containment wall being collapsible to reduce the overall length of the containment device; and
the containment wall being collapsible to reduce the overall length of the containment device.

* * * * *